United States Patent
Weusthuis et al.

(10) Patent No.: US 10,443,077 B2
(45) Date of Patent: Oct. 15, 2019

(54) FERMENTATION PROCESS FOR PRODUCING ITACONIC ACID UNDER NITROGEN FREE CONDITIONS

(71) Applicant: DSM IP ASSETS B.V., Heerlen (NL)

(72) Inventors: Ruud Weusthuis, Wageningen (NL);
Kiira Vuoristo, Wageningen (NL);
Gerrit Eggink, Wageningen (NL);
Johan Pieter Marinus Sanders, Wageningen (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/550,894

(22) PCT Filed: Feb. 16, 2016

(86) PCT No.: PCT/EP2016/053249
§ 371 (c)(1),
(2) Date: Aug. 14, 2017

(87) PCT Pub. No.: WO2016/131818
PCT Pub. Date: Aug. 25, 2016

(65) Prior Publication Data
US 2018/0016604 A1    Jan. 18, 2018

Related U.S. Application Data

(60) Provisional application No. 62/116,657, filed on Feb. 16, 2015.

(30) Foreign Application Priority Data

Apr. 22, 2015  (EP) ..................... 15164702

(51) Int. Cl.
*C12P 7/44*  (2006.01)
*C12N 15/52*  (2006.01)
*C12N 9/88*  (2006.01)

(52) U.S. Cl.
CPC .......... *C12P 7/44* (2013.01); *C12N 9/88* (2013.01); *C12N 15/52* (2013.01); *C12Y 401/01006* (2013.01)

(58) Field of Classification Search
None
See application file for complete search history.

(56) References Cited

U.S. PATENT DOCUMENTS

| 6,265,186 | B1 | 7/2001 | Swinkels et al. |
| 2010/0285546 | A1 | 11/2010 | Liao et al. |
| 2011/0053232 | A1 | 3/2011 | Wang et al. |

FOREIGN PATENT DOCUMENTS

| EP | 0 481 008 | 4/1992 |
| EP | 0 635 574 | 1/1995 |
| WO | WO 90/14423 | 11/1990 |
| WO | WO 98/46772 | 10/1998 |
| WO | WO 99/60102 | 11/1999 |
| WO | WO 00/37671 | 6/2000 |
| WO | WO 08/000632 | 1/2008 |
| WO | WO 09/014437 | 1/2009 |
| WO | WO 2014/178717 | 11/2014 |

OTHER PUBLICATIONS

Levinson et al. Enzyme and Microbial Technology 39 (2006), 824-827. (Year: 2006).*
International Search Report and Written Opinion of the ISA for PCT/EP2016/053249, dated Jul. 8, 2016, 21 pages.
Vuoristo et al., "Metabolic engineering of itaconate production in *Escherichia coli*", Applied Microbiology and Biotechnology, vol. 99, No. 1, Oct. 3, 2014, pp. 221-228.
Vuoristo et al., "Metabolic engineering of the mixed-acid fermentation pathway of *Escherichia coli* for anaerobic production of glutamate and itaconate", AMB Express, vol. 5, 61, Sep. 17, 2015, pp. 1-11.
Datsenko, K. A. and Wanner, B. L., "One-step inactivation of chromosomal genes in *Escherichia coli* K-12 using PCR products," PNAS 97(12):6640-6645 (2000).
Dwiarti, L., et al., "Purification and Characterization of cis-Aconitic Acid Decarboxylase from *Aspergillus terreus* TN484-M1," Journal of Bioscience and Bioengineering 94(1):29-33 (2002).
Li, A., et al., "A clone-based transcriptomics approach for the identification of genes relevant for itaconic acid production in *Aspergillus*," Fungal Genetics and Biology 48:602-611 (2011).
Jürgen, B., et al., "Quality control of inclusion bodies in *Escherichia coli*," Microbial Cell Factories 9(1):41, 13 pages (2010).
Castaño-Cerezo, S., et al., "An insight into the role of phosphotransacetylase (pta) and the acetate/acetyl-CoA node in *Escherichia coli*," Microbial Cell Factories 8:54, 19 pages (2009).

* cited by examiner

*Primary Examiner* — Christian L Fronda
(74) *Attorney, Agent, or Firm* — Nixon & Vanderhye P.C.

(57) ABSTRACT

The present invention relates to a method for the production of itaconic acid, which method comprises fermenting a recombinant cell capable of producing itaconic acid in a suitable fermentation medium, thereby to produce itaconic acid, wherein: (a) the recombinant cell: (i) overexpresses cis-aconitate decarboxylase; and (ii) overexpresses a part of the citric acid cycle and/or has reduced activity of a native metabolic route to acetate and/or lactate; and, optionally, (b) the fermentation is carried out under anaerobic conditions.

10 Claims, 7 Drawing Sheets
Specification includes a Sequence Listing.

FERMENTATION PROCESS FOR PRODUCING ITACONIC ACID UNDER NITROGEN FREE CONDITIONS

This application is the U.S. national phase of International Application No. PCT/EP2016/053249 filed 16 Feb. 2016, which designated the U.S. and claims priority to EP Patent Application No. 15164702.1 filed 22 Apr. 2015, and claims the benefit of U.S. Provisional Application No. 62/116,657 filed 16 Feb. 2015, the entire contents of each of which are hereby incorporated by reference.

FIELD OF THE INVENTION

The present invention relates to a method for the production of itaconic acid by fermentation. The invention further relates to a fermentation broth comprising itaconic acid obtainable by such a method and to a method for production of a pharmaceutical, cosmetic, food, feed or chemical product using itaconic acid obtainable by the method for the production of itaconic acid. The invention also relates to a recombinant cell capable of producing itaconic acid.

BACKGROUND TO THE INVENTION

Itaconic acid, an unsaturated C5 dicarboxylic acid produced by various microorganisms, can be used as a precursor of many industrially relevant compounds in chemical and pharmaceutical industries. It is especially of interest for the production of polymers, because of its potential as a substitute for acrylic and methacrylic acid used for the production of plastics. Acrylic and methacrylic acid are severely irritating and corrosive to the skin and the resiratory tract Itaconinc acid on the other hand is non toxic and readily biodegradable and for these reasons the need for itaconic acid in the above-mentioned productions is expected to increase.

Current fermentation processes for the production of itaconic acid from sugar are executed aerobically using oxygen as the terminal electron acceptor. The productivity of aerobic processes is usually low (<1 g/l/h) and is determined by the oxygen transfer rate and/or the cooling capacity required for dissipating the heat that is generated. The yield of aerobic processes is limited, because the substrate can be completely oxidized by respiration. Moreover respiration generates a lot of metabolic energy, resulting in the conversion of substrate into microbial biomass, which also lowers the product yield.

Accordingly, there is a need to further improve itaconic acid production processes so that economically viable, large scale production may be achieved in industrial bioreactors.

SUMMARY OF THE INVENTION

It is known in the art that itaconic acid can be produced aerobically by *E. coli* by overexpressing cis-aconitate decarboxylase (cadA) from *Aspergillus terreus*. Herein, it is demonstrated that itaconic acid production by *E. coli* is improved by: enhancing the availability of precursors by overexpression of the first part of the citric acid cycle (citrate synthase and aconitase, for example citrate synthase (gltA) and aconitase (acnA) from *C. glutamicum*), i.e. by overexpression of the genes encoding the enzymes involved in the first part of the citric acid cycle; and elimination of the native metabolic routes to acetate and lactate by inactivating the genes encoding phosphate acetyltransferase (pta)) and lactate dehydrogenase (ldhA).

The conversion of glucose to itaconate is an oxidation reaction, resulting in the net reduction of the NAD cofactor. Respiration is used to regenerate NAD under aerobic conditions. Under anaerobic conditions alternative methods have to be employed for cofactor regeneration.

Further demonstrated is improved itaconate production in the anaerobic fermentative production of itaconate in *E. coli* by co-producing ethanol and either formate or $H_2$ and $CO_2$. Unexpectedly, strains started to produce significant amounts of glutamate under anaerobic conditions when the itaconate pathway was introduced. Therefore, strategies to eliminate glutamate formation may be used to further increase itaconate production.

Accordingly, the invention relates to a method for the production of itaconic acid or a fermentation broth comprising itaconic acid, which method comprises fermenting a recombinant cell capable of producing itaconic acid in a suitable fermentation medium, for example under conditions which lead to the production of itaconic acid, thereby to produce itaconic acid, wherein:
 (a) the recombinant cell: (i) overexpresses cis-aconitate decarboxylase; and (ii) overexpresses a part of the citric acid cycle and/or has reduced activity of a native metabolic route to acetate and/or lactate; and, optionally,
 (b) the fermentation is carried out under anaerobic conditions.

Such a process may optionally comprise recovering the itaconic acid.

The invention also relates to a fermentation broth comprising itaconic acid obtainable by the method of the invention. The fermentation broth may comprise itaconic acid in the form of itaconic acid secreted into the broth from a recombinant cell of the invention and/or itaconic acid comprised within a recombinant cell of the invention. The broth may comprise a recombinant cell of the invention or may be a broth from which such cells have been removed.

Further, the invention relates to a method for the production of a pharmaceutical, cosmetic, food, feed or chemical product which method comprises: (a) preparing itaconic acid by the method of the invention and; (b) preparing the pharmaceutical, cosmetic or chemical product using said itaconic acid.

In addition, the invention relates to a recombinant cell capable of producing itaconic, wherein the recombinant cell: (i) overexpresses cis-aconitate decarboxylase; and (ii) overexpresses a part of the citric acid cycle and/or has reduced activity of a native metabolic route to acetate and/or lactate.

DESCRIPTION OF THE SEQUENCE LISTING

SEQ ID NO: 1 sets out the sequence of the ldhA flank F primer used for ldhA deletion.
SEQ ID NO: 2 sets out the sequence of the ldhA flank R primer used for ldhA deletion.
SEQ ID NO: 3 sets out the sequence of the ldhA check F primer used for PCR verification.
SEQ ID NO: 4 sets out the sequence of the ldhA check R primer used for PCR verification.
A description of the sequences is also set out in Table 2.

DETAILED DESCRIPTION OF THE INVENTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The invention relates to a method for the production of itaconic acid, and optionally, glutamate, or to a method for the production of a fermentation broth comprising itaconic acid, and optionally glutamate, in which a recombinant cell capable of producing itaconic acid is fermented in a suitable fermentation medium. Fermentation of the recombinant cell may be carried out under conditions which lead to the production of itaconic acid. The invention also relates to the recombinant cell capable of producing itaconic acid itself. Herein, a "recombinant" cell indicates that the cell has been modified by the introduction of a heterologous nucleic acid or protein or the alteration of a native nucleic acid or protein, or that the cell is derived from a cell so modified.

Thus, for example, a recombinant cell of the invention may express a gene that is not found within the native (non-recombinant) form of the cell or express native genes that are otherwise abnormally expressed, under-expressed or not expressed at all. A recombinant cell may, in comparison to a non-recombinant form of the cell, under-express or not express at all a native gene, for example, such that it has reduced activity in a given metabolic pathway. That is to say, the enzyme encoded by a said native gene may be produced in a lesser amount, not produced at all and/or may have a lower or absent biological activity in comparison with a non-recombinant form of the cell. Thus, a recombinant cell of the invention/cell suitable for use in a method of the invention may overexpress a non-native or native gene and/or under-express a native gene The recombinant cell of the invention/cell used in a method of the invention is one which:
(i) overexpresses cis-aconitate decarboxylase; and
(ii) overexpresses a part of the citric acid cycle and/or has reduced activity of a native metabolic route to acetate and/or lactate.

Overexpression of a part of the citric acid cycle implies that one or more of the genes encoding enzymes involved in a part of the citric acid cycle are overexpressed. Reduced activity of a native metabolic route to acetate and/or lactate implies that such a native metabolic route is down-regulated.

In the context of the present invention, a native metabolic route is down-regulated in a recombinant host cell when at least one gene involved in the metabolic route is abnormally expressed, under-expressed or not expressed at all so that the enzyme encoded by said gene is produced in a lesser amount, not produced at all and/or has a lower or absent biological activity in a given metabolic pathway in comparison to the non-recombinant form of the cell.

Thus, the recombinant cell of the invention/cell used in a method of the invention may be one which:
(i) overexpresses cis-aconitate decarboxylase; and
(iia) overexpresses a part of the citric acid cycle; or
(iib) has reduced activity of a native metabolic route to acetate and/or lactate; or
(iic) overexpresses a part of the citric acid cycle and has reduced activity of a native metabolic route to acetate and/or lactate.

"Overexpression" in the context of this invention indicates that a given nucleic acid sequence and/or amino acid sequence is expressed to a greater degree in a recombinant cell of the invention than a non-recombinant form of the cell, which may typically be a corresponding wild type cell (i.e. a wild type cell of the same species). A nucleic acid and/or polypeptide may be overexpressed in the sense that a nucleic acid and/or polypeptide expressed in the reference cell is expressed to a greater degree in a recombinant cell of the invention (the reference cell may not express the nucleic acid and/or polypeptide at all). Overexpression may occur, for example, via overexpression of a nucleic acid and/or polypeptide which is endogenous (or homologous) to the reference cell. Overexpression may occur, for example, via overexpression of a nucleic acid and/or polypeptide which is exogenous (or heterologous) to the reference cell. That is to say, overexpression may occur, for example, via overexpression of a nucleic acid and/or polypeptide which is natively occurs in the reference cell. Overexpression may occur, for example, via overexpression of a nucleic acid and/or polypeptide which is not present or not expressed at all in the reference cell.

A recombinant cell of the invention/recombinant cell for use in a method of the invention may overexpress at least one exogenous nucleic acid and/or polypeptide and overexpress at least one endogenous nucleic acid and/or polypeptide.

To increase the likelihood that an introduced enzyme(s) is/are expressed in active form in a eukaryotic cell of the invention, the corresponding encoding nucleotide sequence may be adapted to optimise its codon usage to that of the chosen eukaryote host cell. Several methods for codon optimisation are known in the art. A preferred method to optimise codon usage of the nucleotide sequences to that of the eukaryotic cell is a codon pair optimization technology as disclosed in WO2008/000632. Codon-pair optimization is a method for producing a polypeptide in a host cell, wherein the nucleotide sequences encoding the polypeptide have been modified with respect to their codon-usage, in particular the codon-pairs that are used, to obtain improved expression of the nucleotide sequence encoding the polypeptide and/or improved production of the polypeptide. Codon pairs are defined as a set of two subsequent triplets (codons) in a coding sequence.

In a recombinant cell of the invention/recombinant cell for use in a method of the invention, a cis-aconitate decarboxylase is typically overexpressed. A cis-aconitate decarboxylase (EC 4.1.1.6) is any enzyme that catalyzes the chemical reaction:

$$\text{cis-aconitate} \rightleftharpoons \text{itaconate} + CO_2$$

A suitable cis-aconitate decarboxylase may be one which is obtainable from, that is to say derivable from or found in, *Aspergillus terreus* (Dwiarti et al., J. Bioscience and Bioengineering, 94 (1):29-33, 2002 and WO 2009/014437).

In a recombinant cell of the invention/recombinant cell for use in a method of the invention, overexpression of a part of the citric acid cycle may be overexpression of a citrate synthase and/or overexpression of an aconitase.

A suitable citrate synthase (E.C. 2.3.3.1 [previously 4.1.3.7]) may be any enzyme that catalyzes the condensation reaction of the two-carbon acetate residue from acetyl coenzyme A and a molecule of four-carbon oxaloacetate to form the six-carbon citrate:

$$\text{acetyl-CoA} + \text{oxaloacetate} + H_2O \rightarrow \text{citrate} + \text{CoA-SH}$$

A suitable citrate synthase may be that encoded by the gltA gene from *Corynebacterium glutamicum* (eg. Gen Bank NP_600058.1).

An aconitase (aconitate hydratase; EC 4.2.1.3) is an enzyme that catalyses the stereo-specific isomerization of citrate to isocitrate via cis-aconitate in the tricarboxylic acid cycle, a non-redox-active process.

A suitable aconitase may be that encoded by the acnA gene from *Corynebacterium glutamicum* (eg. Gen Bank NP_600755.1).

A recombinant cell of the invention/recombinant cell for use in a method of the invention may have reduced activity of a native metabolic route to acetate and/or lactate. "Reduced activity" indicates that the recombinant cell is modified such that less acetate and/or lactate is produced in the recombinant cell as compared with a non-recombinant form of the cell.

Such reduced activity may be achieved by reducing the activity of one or more enzymes involved in the native metabolic route to acetate and/or lactate. "Reduced activity" in this sense indicates that a recombinant cell has been modified, preferably in its genome, to result in a deficiency in the production of one or more enzymes involved in the native metabolic route to acetate and/or lactate. Such a recombinant cell may be modified, preferably in its genome, to result in a phenotypic feature wherein the cell: a) produces less of the enzyme or produces substantially none of the enzyme and/or b) produces an enzyme having a decreased activity or decreased specific activity or an enzyme having no activity or no specific activity and combinations of one or more of these possibilities as compared to a non-modified form of the recombinant cell.

In a recombinant cell of the invention/recombinant cell for use in a method of the invention, reduced activity of a native metabolic route to acetate may be a result of reduced activity of a phosphate acetyltransferase, for example by deleting, disrupting or inactivating a gene encoding that enzyme such as the pta gene or homolog/ortholog of that gene depending on the species of the recombinant cell.

In a recombinant cell of the invention/recombinant cell for use in a method of the invention, reduced activity of a native metabolic route to acetate may be a result of reduced activity of a lactate dehydrogenase, for example by deleting, disrupting or inactivating a gene encoding that enzyme such as the ldhA gene or homolog/ortholog of that gene depending on the species of the recombinant cell.

In the method of the invention, production of itaconic acid may be accompanied by: ethanol and formate (or hydrogen gas and $CO_2$) production; or succinate.

In the method of the invention, glutamate production may be repressed. "Repression" of glutamate indicates that steps are taken so that production of glutamate takes place in the method of the invention to a lesser extent that would the case in the absence of those steps. Such steps may be modifications to the recombinant cell or may be specific steps taken in the process itself to repress glutamate production. For example, a repression of glutamate production may be carried out by carrying out the fermentation under nitrogen free conditions.

The recombinant cell of the invention/recombinant cell for use in a method of the invention may be a prokaryotic, an archael cell or a eukaryotic host cell. A recombinant cell of the invention/recombinant cell for use in a method of the invention may be a prokaryotic cell. Preferably, the prokaryotic cell is a bacterial cell. The term "bacterial cell" includes both Gram-negative and Gram-positive microorganisms. Suitable bacteria may be selected from e.g. *Escherichia, Anabaena, Caulobactert, Gluconobacter, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus, Methylobacterium, Staphylococcus* or *Streptomyces*. Preferably, the bacterial cell is selected from the group consisting of *B. subtilis, B. amyloliquefaciens, B. licheniformis, B. puntis, B. megaterium, B. halodurans, B. pumilus, G. oxydans, Caulobactert crescentus* CB 15, *Methylobacterium extorquens, Rhodobacter sphaeroides, Pseudomonas zeaxanthinifaciens, Paracoccus denitrificans, E. coli, C. glutamicum, Staphylococcus carnosus, Streptomyces lividans, Sinorhizobium melioti* and *Rhizobium radiobacter.*

A recombinant cell of the invention/recombinant cell for use in a method of the invention may be a eukaryotic cell. Preferably, the eukaryotic cell is a fungal, or algal cell.

A suitable fungal cell may be a yeast cell or a filamentous fungal cell.

Suitable yeast cells include those such as *Candida, Hansenula, Kluyveromyces, Pichia, Saccharomyces, Schizosaccharomyces,* or *Yarrowia* strain. More preferably a *Kluyveromyces lactis, Saccharomyces cerevisiae, Hansenula polymorpha, Yarrowia lipolytica* or *Pichia pastoris*, or a filamentous fungal cell.

Suitable filamentous fungal cell include all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation. Filamentous fungal strains include, but are not limited to, strains of *Acremonium, Agaricus, Aspergillus, Aureobasidium, Chrysosporium, Coprinus, Cryptococcus, Filibasidium, Fusarium, Geosmithia, Humicola, Magnaporthe, Mucor, Myceliophthora, Neocallimastix, Neurospora, Paecilomyces, Penicillium, Piromyces, Panerochaete, Pleurotus, Rasamsonia, Schizophyllum, Talaromyces, Thermoascus, Thermomyces, Thielavia, Tolypocladium,* and *Trichoderma.* For example, a species of *Aspergillus niger, Acremonium alabamense, Acremonium chrysogenum, Aspergillus awamori, Aspergillus foetidus, Aspergillus sojae, Aspergillus fumigatus, Talaromyces emersonii, Talaromyces thermophilus, Thermomyces lanuginosus, Thermoascus thermophilus, Thermoascus aurantiacus, Thermoascus crustaceus, Rasamsonia emersonii, Rasamsonia byssochlamyoides, Rasamsonia argillacea, Rasamsonia brevistipitata, Rasamsonia cylindrospora, Aspergillus oryzae, Chrysosporium lucknowense, Fusarium oxysporum, Myceliophthora thermophila, Trichoderma reesei, Thielavia terrestris* or *Penicillium chrysogenum.* Most preferred species are *Aspergillus niger* or *Penicillium chrysogenum.*

Several strains of filamentous fungi are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL) *Aspergillus niger* CBS 513.88, *Aspergillus oryzae* ATCC 20423, IFO 4177, ATCC 1011, ATCC 9576, ATCC14488-14491, ATCC 11601, ATCC12892, *P. chrysogenum* CBS 455.95, *Penicillium citrinum* ATCC 38065, *Penicillium chrysogenum* P2, *Talaromyces emersonii* CBS 124.902, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* C1, Garg 27K, VKM-F 3500 D, ATCC44006 and derivatives thereof.

The method of the invention for the preparation of itaconic acid or for the preparation of a fermentation broth comprising itaconic acid comprises fermenting a recombinant cell, for example a recombinant prokaryotic cell or recombinant eukaryotic cell, as described herein in the presence of a suitable fermentation medium under anaerobic conditions. Suitable fermentation media are known to the person skilled in the art. Fermentation of the recombinant cell may be carried out under conditions which lead to the production of itaconic acid. The method of the invention may be carried out in the presence or absence of oxygen. Typically, the method is carried out under anaerobic conditions.

For the purposes of this invention, an anaerobic fermentation process may be herein defined as a fermentation process run in the absence of oxygen or in which substantially no oxygen is consumed, preferably less than 5, 2.5 or 1 mmol/L/h, and wherein organic molecules serve as both electron donor and electron acceptors. The fermentation process according to the present invention may also first be run under aerobic conditions and subsequently under anaerobic conditions. Anaerobic conditions are typically used in the production phase (production of the itaconic acid).

The fermentation process of the invention may also be run under oxygen-limited, or micro-aerobic, conditions which are, for the purposes of this invention, considered to be anaerobic processes. Alternatively, the fermentation process may first be run under aerobic conditions and subsequently under oxygen-limited conditions. An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used.

The process for the production of itaconic acid according to the present invention may be carried out at any suitable pH between 1 and 9. Preferably, the pH in the fermentation broth is between 2 and 7. It may be advantageous to be able to carry out the process according to the present invention at a low pH, for example at a pH equal to or below the pKa, typically the lowest pKa, of itaonic acid, since this may help to prevent bacterial contamination. In addition, since the pH drops during itaconic acid production, a lower amount of titrant is needed to keep the pH at a desired level.

A suitable temperature at which the process according to the present invention may be carried out is between 5 and 60° C., preferably between 10 and 50° C., more preferably between 15 and 35° C., more preferably between 18° C. and 30° C. The person skilled in the art knows which optimal temperatures are suitable for fermenting a specific yeast cell.

In a method of the invention for the production of itaconic acid, the acid may be secreted into the fermentation broth and/or present in the recombinant cell used in the invention. Thus, the invention also provides a fermentation broth comprising itaconic acid obtainable by a method according to the invention. The broth may comprise: itaconic acid which has been secreted from a recombinant cell: itaconic acid comprised within a recombinant cell of the invention; itaconic acid which has been released from a recombinant cell following treatment of the cell to cause disruption of the cell and release of itaconic acid; or a mixture of any thereof.

Preferably, in the method of the invention, the itaconic acid is recovered from the fermentation broth by a suitable method known in the art, for instance by extraction or crystallisation. A recombinant cell of the invention may need to be disrupted to allow for release of itaconic acid.

Preferably, the itaconic acid or an ester of itaconic acid that is prepared in the process according to the present invention is further converted into a desirable product, such as a pharmaceutical, cosmetic, food, feed or chemical product. In particular, itaconic acid may be further converted into a polymer.

Thus, the invention provides a method for the production of a pharmaceutical, cosmetic, food, feed or chemical product which method comprises: (a) preparing itaconic acid by a method according to the invention and; (b) preparing the pharmaceutical, cosmetic, food, feed or chemical product using said itaconic acid.

Standard genetic techniques, such as overexpression of enzymes in host cells, genetic modification of host cells, or hybridisation techniques, are known methods in the art, such as described in Sambrook and Russel (2001) "Molecular Cloning: A Laboratory Manual ($3^{rd}$ edition), Cold Spring Harbor Laboratory, *Cold Spring Harbor Laboratory Press*, or F. Ausubel et al, eds., "Current protocols in molecular biology", Green Publishing and Wiley Interscience, New York (1987). Methods for transformation, genetic modification etc. of fungal host cells are known from e.g. EP-A-0 635 574, WO 98/46772, WO 99/60102 and WO 00/37671, WO90/14423, EP-A-0481008, EP-A-0635 574 and U.S. Pat.

No. 6,265,186. Accordingly, preparation of a recombinant cell suitable for use in the invention is well known to those skilled in the art.

Embodiments of the Invention

1. A method for the production of itaconic acid, which method comprises fermenting a recombinant cell capable of producing itaconic acid in a suitable fermentation medium, thereby to produce itaconic acid, wherein:
   (a) the recombinant cell: (i) overexpresses cis-aconitate decarboxylase; and (ii) overexpresses a part of the citric acid cycle and/or has reduced activity of a native metabolic route to acetate and/or lactate; and, optionally,
   (b) the fermentation is carried out under anaerobic conditions.
2. A method according to embodiment 1, wherein the cis-aconitate decarboxylase is one obtainable from, such as derivable from or found in or isolated from, *Aspergillus terreus*.
3. A method according to embodiment 1 or 2, wherein overexpression of a part of the citric acid cycle is overexpression of a citrate synthase and/or overexpression of an aconitase.
4. A method according to any one of embodiments 1 to 3, wherein reduced activity of a native metabolic route to acetate is reduced activity of a phosphate acetyltransferase.
5. A method according to any one of embodiments 1 to 4, wherein reduced activity of a native metabolic route to lactate is reduced activity of a lactate dehydrogenase.
6. A method according to any one of embodiments 1 to 5, wherein production of itaconic acid is accompanied by ethanol and formate (or hydrogen gas and $CO_2$) production.
7. A method according to any one of embodiments 1 to 6, wherein glutamate production is repressed, preferably wherein Repression of glutamate production is achieved by taking steps so that production of glutamate takes place in the method to a lesser extent that would the case in the absence of those steps, more preferably wherein repression of glutamate production is carried out by carrying out the fermentation under nitrogen free conditions.
8. A method according to any one of embodiments 1 to 7, wherein the recombinant cell is a prokaryotic or a eukaryotic cell.
9. A method according to embodiment 8, wherein the cell is a bacterial cell, such as *E. coli*, or a yeast cell, such as *S. cerevisiae*.
10. A method according to any one of the preceding embodiments which comprises recovery of the itaconic acid.
11. A fermentation broth comprising itaconic acid obtainable by a method according to any one of embodiments 1 to 10.
12. A method for the production of a pharmaceutical, cosmetic, food, feed or chemical product which method comprises: (a) preparing itaconic acid by a method according to any one of embodiments 1 to 10 and; (b) preparing the pharmaceutical, cosmetic, food, feed or chemical product using said itaconic acid.
13. A recombinant cell capable of producing itaconic acid, wherein the recombinant cell: (i) overexpresses cis-aconitate decarboxylase; and (ii) overexpresses a part of the citric acid cycle and/or has reduced activity of a native metabolic route to acetate and/or lactate.
14. A recombinant cell according to embodiment 13 as defined in any one of embodiments 1 to 5, 8 or 9.
15. A method for the production of itaconic acid, which method comprises fermenting a recombinant cell capable of producing itaconic acid in a suitable fermentation medium, thereby to produce itaconic acid, wherein the recombinant cell is one according to embodiment 13 or 14.
16. A method according to embodiment 15, wherein the fermentation is carried out under anaerobic conditions, preferably wherein fermentation carried out under anaerobic conditions means a fermentation process run in the absence of oxygen or in which substantially no oxygen is consumed or a fermentation process run under oxygen limited, or micro-aerobical, conditions.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

Methods

Bacterial Strains and Plasmids

The bacterial strains and plasmids used in this study are listed in Table 1.

Deletion of Phosphate Acetyltransferase (pta) and Lactate Dehydrogenase (ldhA) Genes The gene encoding lactate dehydrogenase (ldhA) was inactivated in *E. coli* BW25113 Δpta by using the Lambda red-mediated gene replacement method described by (Datsenko and Wanner (2000), Proceedings of the National Academy of Sciences of the United States of America 97(12):6640-6645). Shortly, *E. coli* BW25113 Δpta was transformed with pKD46 and cultured in the presence of L-arabinose to induce λ-red recombinase expression, which is an inducer for recombination. The target gene ldhA was replaced by a kanamycin resistance gene flanked by flippase recognition target (FRT) sites. For this, a deletion cassette containing a kanamycin resistance gene with FRT sites was amplified from pKD4 by using Phusion High Fidelity DNA Polymerase (Thermo Scientific) and primers that contain 50 bp targeting flanks to the ldhA region in the genome (Table 2) and transformed into *E. coli* BW25113 Δpta (pKD46). Transformants were screened for their proper genotype by selecting for kanamycin resistance and colony PCR (GoTaq Green polymerase, Promega) using primers that flank the target gene. The phenotype was verified in liquid cultures. The kanamycin resistance gene was subsequently eliminated by using the temperature-sensitive helper plasmid pCP20 encoding the flippase (FLP), followed by curing of the temperature sensitive plasmids by culturing strains at 42° C. for 16 hours.

Site-specific Integration of the λDE3 Prophage

Site-specific integration of the λDE3 prophage into *E. coli* BW25113 and into its derivative *E. coli* BW25113 Δpta ΔldhA was done using the λDE3 Lysogenization Kit (Novagen). The integration of the λDE3 prophage and expression of T7 polymerase in strains were verified according to the protocol in the kit. Besides, the functional expression of T7 polymerase was confirmed by transforming the strains with pET101/D/lacZ. The transformants were able to cleave 5-bromo-4-chloro-3-indolyl-β-D-galactopyranoside (X-gal) after induction with isopropyl-beta-D-thiogalactopyranoside (IPTG).

Construction of pACYC Expression Vectors

The expression vector pACYCDuet-1 (Novagen) was used to express the genes cadA (NCBI Reference Sequence ID: BAG49047.1), acnA (ID: NP_600755.1), and gltA (ID: NP_600058.1) under the transcriptional control of the T7 promoter. All genes were codon-optimized according to the algorithm of OptimumGene™ (GenScript) and synthesized by GenScript, USA. The sequences of the codon-optimized cadA, acnA, and gltA can be retrieved from GenBank (ID: KM464677, ID: KM464678, ID: KM464679, respectively. cadA was ligated between the NcoI-HindIII restriction sites in MCS1 of pACYCDuet-1, yielding pKV-C. acnA and gltA were respectively ligated between the NdeI-XhoI and XhoI-PacI sites in MCS2 of pKV-C, yielding pKV-CGA, Table 1. An additional ribosomal binding site (rbs), identical to those in pACYCDuet-1, was introduced upstream of gltA gene. The expression vector pKV-GA was derived from pKV-CGA by cloning the acnA and gltA containing part of pKV-CGA in pACYCDuet-1.

Cultivation Conditions

Culture Media

For plasmid construction and gene expression analysis, E. coli strains were cultured on Luria-Bertani (LB) agar plates or in LB liquid medium at either 30° C. or 37° C. Recombinants harbouring temperature-sensitive plasmids were cultured at either 30° C. for cultivation or 42° C. to cure the selection markers. Expression of lacZ was detected by blue/white screening in agar plates on top of which 40 µl of 20 mg/ml X-gal in dimethyl sulfoxide and 40 µl of 1 M IPTG were spread on top of the plates. When needed, medium and plates were supplemented with ampicillin (50 µg/mL) or chloramphenicol (35 µg/mL). Induction of gene expression in liquid cultures was started by the addition of 1 mM of IPTG when the optical density at 600 nm ($OD_{600}$) of the culture reached approximately 0.4.

The other cultivations were done in M9 Minimal medium (MM), which contained per 1 liter: 200 mL 5×M9 Minimal Salts (BD Difco) supplemented with 50 mmoles of glucose, 2 mmoles of MgSO4, 0.1 mmoles of $CaCl_2$, 15 mg of thiamine, and 0.30 mg of selenite. Medium was buffered with 0.1 M 3-(N-morpholino) propanesulfonic acid (MOPS) and the pH was adjusted to 6.9 with NaOH.

Cultivation in Bioreactors (Aerobic)

E. coli BW25113 (DE3) and E. coli BW25113 (DE3) Δpta-ΔldhA containing either pEV, pKV-C or pKV-CGA were cultivated at 30° C. in 0.5 L Mini Bioreactors, connected to myControl controller units (Applikon, The Netherlands) with a working volume of 400 ml. The pH was maintained at 6.9 by the automated addition of 2 M NaOH. Cultures were continuously stirred at 1200 rpm and sparged with medical air at 400 mL/min. Bioreactors were inoculated with 5% (v/v) of a pre-culture that was grown in a 250 mL Erlenmeyer flasks with 50 mL of MM at 250 rpm and 30° C. for 24 hours. Samples of 2 mL were regularly taken to determine the $OD_{600}$ of the cultures and the concentrations of substrate and products.

Cultivation in Bioreactors (Anaerobic)

E. coli BW25113 (DE3) and E. coli BW25113 (DE3) Δpta-ΔldhA containing either pEV, pKV-C or pKV-CGA were cultivated at 30° C. in 0.5 L Mini Bioreactors, connected to myControl controller units (Applikon, The Netherlands) with a working volume of 400 ml. The pH was maintained at 6.9 by the automated addition of 2 M NaOH. Cultures were stirred at 400 rpm and sparged with nitrogen at 16 mL/min for 17 hours, after which the stirring speed was increased to 800 rpm and the sparging rate was increased to at 35 mL/min. Bioreactors were inoculated with 5% (v/v) of a pre-culture that was grown at 30° C. in a 250 mL Erlenmeyer flasks with 50 mL of MM at 250 rpm for 24 hours. Samples of 2 mL were regularly taken to determine the $OD_{600}$ of the cultures and the concentrations of substrate and products.

Enzymatic Assays

For enzymatic assays, 50 mL of bioreactor culture was harvested by centrifugation (5 min, 7745×g) after 17 hours of cultivation in the presence of IPTG and washed with MM. Cell free extracts (CFE) were made according to the Y-PER Yeast Protein Extraction Reagent kit instructions (Thermo Scientific). Protein concentrations were determined by using the Total Protein Kit, Micro Lowry, Peterson's Modification (Sigma Aldrich).

The activity of cis-aconitate decarboxylase (CadA) was measured by using a method adapted from (Dwiarti et al. (2002) Journal of Bioscience and Bioengineering 94(1):29-33) and (Li et al. (2011) Fungal genetics and biology 48(6)): CFE's were incubated with 17 mM of cis-aconitate in 200 mM sodium phosphate buffer (pH 6.2) for 10 min at 30° C. Reactions were terminated by adding 1 M HCl. Supernatants were analyzed for itaconate formation by HPLC.

The activity of aconitase was measured by monitoring the formation of cis-aconitate at 240 nm in a UV-Vis Spectrophotometer (UV-1650PC SHIMADZU) using an extinction coefficient for cis-aconitate of 3.5 $mM^{-1}$ $cm^{-1}$ (Baumgart and Bott 2011). The assays were performed at 30° C. in 100 mM Tris-HCl buffer (pH 8.0) and 20 mM trisodium citrate as a substrate.

Citrate synthase activity was determined by monitoring the hydrolysis of the thioester of acetyl coenzyme A (acetyl-CoA), which results in the formation of CoA. The thiol group of CoA reacts with 5,5'-dithiobis-(2-nitrobenzoic acid (DTNB) in the reaction mixture to form 5-thio-2-nitrobenzoicacid (TNB). The formation of TNB was measured at 412 nm by using 13.6 $mM^{-1}$ $cm^{-1}$ as extinction coefficient at 30° C. according to (Morgunov and Srere 1998) with minor adjustments. The reaction mixture contained 0.31 mM acetyl-CoA, 0.5 mM oxaloacetate, 0.1 mM DTNB, and ca. 0.25% Triton X-100 in 100 mM Tris-HCl (pH 8.0).

Analytical Methods

The cell density was determined by measuring the $OD_{600}$ by using a spectrophotometer (Dr. Lange XION 500).

The concentrations of glucose and organic acids were determined by using HPLC by using a Dionex Ultimate 3000 (Thermo Fisher) equipped with an RI detector (Shodex, RI-101) and a UV detector (Dionex, 3400 RS at 210 nm). The samples were separated on a Micro Guard Cation H pre-column (30×4.6 mm, Biorad) and an Aminex HPX-87H column (300×7.8 mm, Biorad) at 35° C., using 0.6 mL/min of 5 mM $H_2SO_4$ as an eluent.

The concentrations of glutamate and alanine were determined by using UPLC Dionex RSLC system with an Ulti-Mate 3000 Rapid Separation pump as described by Meussen et al. (2014, *Food Analytical Methods*, 7:1047-1055).

The concentrations of $CO_2$ and $H_2$ in the off-gas of the bioreactors were determined by using BlueSens Off-Gas Sensors (Gas Sensor, GmbH).

Itaconate Production in Absence of Ammonium

Figure 1:
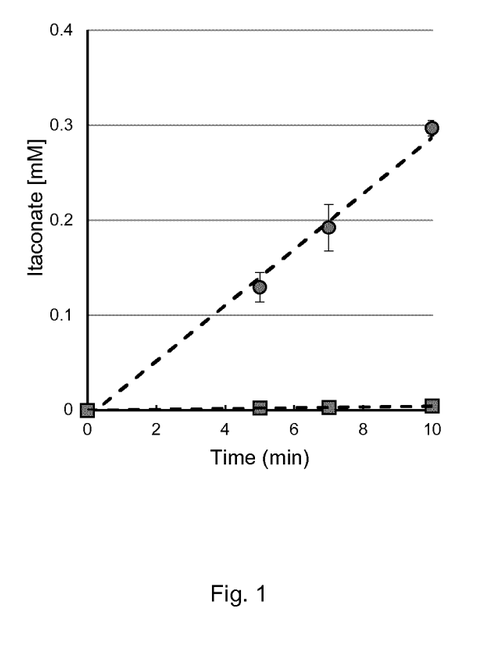
FIG. 1 shows conversion of cis-aconitate to itaconate in CFE of *E. coli* BW25113 (DE3) (pKV-C) that was cultured in bioreactors at either 30° C. (circles) or 37° C. (squares). Protein concentrations in the assay mixtures were 5.8 and 4.3 mg/mL, respectively. The activities of CadA were derived from the slopes of the lines.

To monitor itaconate production in the absence of ammonium, 50 mL of bioreactor culture was harvested by centrifugation (5 min, 7745×g) after 32 hours of cultivation in the presence of IPTG. The culture was washed and resuspended in 40 mL nitrogen-free phosphate buffer (NF-PB), which consisted of 50 mM sodium phosphate (pH 7.0) with 100 mM MOPS and 60 mM glucose. Control samples were washed and resuspended in 40 mL MM with 50 mM glucose. Cultures were transferred to anaerobic serum bottles and cultured at 150 rpm and 30° C. for 24 hours. Samples of 2 mL were regularly taken to determine the $OD_{600}$ of the cultures and the concentrations of substrate and products.

at lower temperatures. When *E. coli* BW25113 (DE3) (pKV-C) was grown in MM in pH-controlled bioreactors at 37°, CadA could be detected in CFE with a specific activity of 0.03 U/mg. The activity was further increased to 0.38 U/mg when the cultivation temperature was lowered to 30° C. (FIG. 1). SDS-PAGE analysis showed that the amount of soluble protein had increased by these measures (data not shown).

TABLE 1

*E. coli* strains and plasmids used in this study

| Strains | | |
|---|---|---|
| BW25113 | lacIq rrnBT14 ΔlacZ WJ16 hsdR514 Δara BADAH33 Δrha BADLD78 | CGSC[1] |
| BW25113 (DE3) | BW25113 DE3 T7 RNA polymerase | This study |
| BW25113 Δpta | BW25113 Δpta - 779::kan | CGSC |
| BW25113 (DE3) Δpta ΔldhA | BW25113 Δpta ΔldhA DE3 T7 RNA polymerase | This study |
| Plasmids | | |
| pET101/D/lacZ | pBR322 ori lacI T7 AmpR | Invitrogen |
| pKD46 | AmpR plasmid with temperature-sensitive replication and arabinose induction of λ-red recombinase | CGSC |
| pKD4 | KanR plasmid with R6K-γ replicon | CGSC |
| pCP20 | AmpR and CmR plasmid with temperature-sensitive replicon and thermal induction of FLP synthesis | CGSC |
| pEV | pACYCDuet-1 overexpression vector using T7 promoter capable to carry two multiple cloning sites, CmR | Novagen |
| pKV-C | pACYCDuet-1 derivative, synthetic cadA gene | This study |
| pKV-CGA | pACYCDuet-1 derivative, synthetic cadA, acnA, and gltA genes | This study |
| pKV-GA | pACYCDuet-1 derivative, synthetic acnA and gltA genes | This study |

[1]The Coli Genetic Stock Center at Yale University

TABLE 2

List of primers used in this study

| Name and description | Sequence |
|---|---|
| | For ldhA deletion |
| ldhA flank F | (SEQ ID NO: 1) aaatattttt agtagcttaa atgtgattca acatcactgg agaaagtctt gtgtaggctg gccatggtcc |
| ldhA flank R | (SEQ ID NO: 2) attggggatt atctgaatca gctccctgg aatgcagggg agcggcaaga atgggaatta gccatggtcc |
| | For PCR verifications |
| ldhA check F | (SEQ ID NO: 3) aaatattttt agtagcttaa atgtg |
| icd check R | (SEQ ID NO: 4) attggggatt atctgaatca gctcc |

Example 1. Heterologous Expression of cadA, acnA, and gltA

Figure 2:
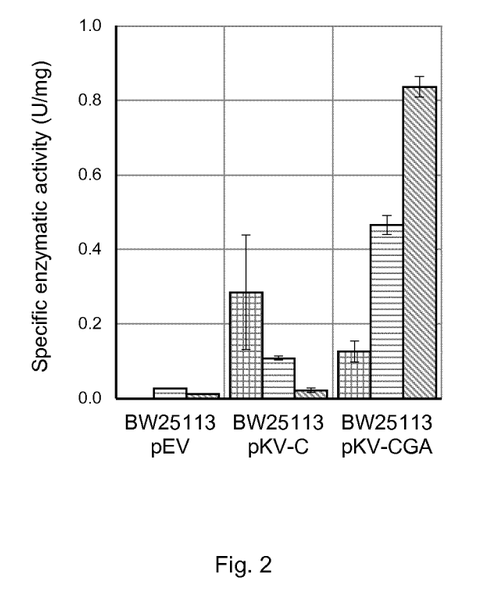
FIG. 2 shows specific enzymatic activities (U/mg) of cis-aconitate decarboxylase (hatched lines), citrate synthase (horizontal lines) and aconitase (diagonal lines) in CFE of *E. coli* BW25113 (DE3) containing either pEV, pKV-C, or pKV-CGA. Strains were cultured in bioreactors at 30° C. on MM medium. The average values and standard deviations (SD) of duplicate parallel studies are given.

Gene cadA from *A. terreus* was codon optimized and expressed in *E. coli* to enable itaconate production. Small amounts of itaconate were produced (below 10 mg/L) when *E. coli* BW25113 (DE3) (pKV-C) was cultivated in LB in shake flask cultures at 37° C., but no detectable CadA activity was found in CFE of these cultures. SDS-PAGE analysis showed that almost all CadA was present in the form of inclusion bodies (data not shown). As inclusion bodies are often associated with fast and high-level expression of heterologous proteins (Jurgen et al. 2010 Microbial Cell Factories 9(1)), two measures were taken to reduce these rates: cultivation in MM instead of LB and cultivation To channel more acetyl-CoA to itaconate, the codon optimized genes encoding citrate synthase (gltA) and aconitase (acnA) from *C. glutamicum* were overexpressed in *E. coli* together with cadA, yielding *E. coli* BW25113 (DE3) (pKV-CGA). The expression levels of the heterologous genes were determined by measuring the activities of the corresponding enzymes in CFE of *E. coli* BW25113 (DE3) strains containing either pEV, pKV-C or pKV-CGA. The activities of citrate synthase and aconitase in CFE's of *E. coli* BW25113 (DE3) (pKV-CGA) increased 4 and 40 times, respectively, compared to the native activities measured in *E. coli* BW25113 (DE3) (pKV-C) (FIG. 2). It appeared that expression of cadA increased the native citrate synthase and aconitase activities in *E. coli* BW25113 (DE3) (pKV-C), as the activities of these enzymes were lower in *E. coli* BW25113 (DE3) (pKV-EV), which might be due to an activating effect of itaconate. Simultaneous expression of gltA and acnA together with cadA resulted in a lower specific CadA activity compared to the *E. coli* BW25113 (DE3) (pKV-C), which is probably due to a dilution effect caused by the overexpression of the two additional genes.

Example 2. Itaconate Production in *E. coli* BW25113 (DE3)

Figure 3:
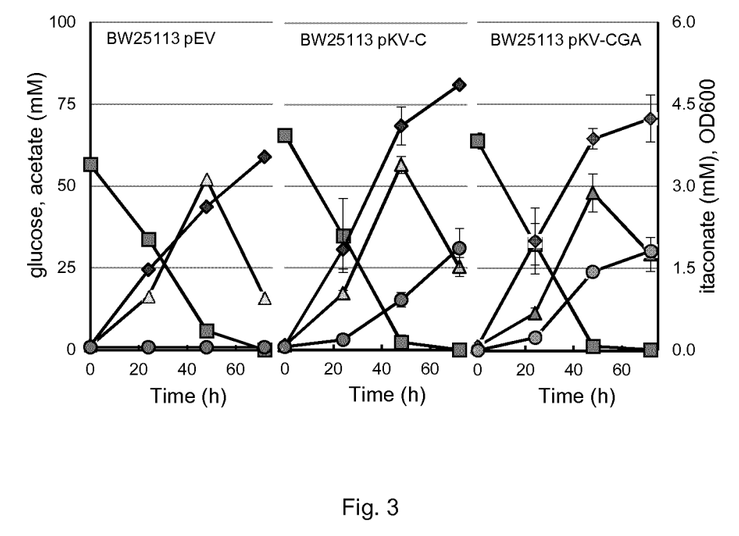
FIG. 3 shows batch cultivation of *E. coli* BW25113 (DE3) containing pEV (left panel), pKV-C (middle panel) and pKV-CGA (right panel) in pH-controlled bioreactors on MM at 30° C. The $OD_{600}$ (diamond) and the concentrations of glucose (squares), acetate (triangles) and itaconate (circles) are indicated.

Itaconate production by *E. coli* BW25113 (DE3) containing either pEV, pKV-C, or pKV-CGA was monitored in pH-controlled bioreactors in MM at 30° C. for 72 hours. Itaconate was produced up to 1.9 mM with both *E. coli* BW25113 (DE3) (pKV-C) and BW25113 (DE3) (pKV-CGA), but not in the control strain (FIG. 3). Overexpression of gltA and acnA together with cadA had no significant impact on itaconate production under these conditions as the production profiles were similar with both pKV-C and pKV-CGA plasmids. This suggests that the availability of precursors is limiting itaconate production.

During growth on glucose, acetate was observed in all cultures after 1 day of cultivation, which accumulated up to 55 mM. When glucose was depleted from the medium, the cells started consuming acetate. In addition, low concentrations (below 5 mM) of ethanol, citrate, pyruvate, lactate, succinate and formate were detected in the medium during cultivation of all strains, and some cis-aconitate (<5 mM) was formed by E. coli BW25113 (DE3) (pKV-C) and BW25113 (DE3) (pKV-CGA) (data not shown). Most of these compounds were only intermediary products and disappeared over time.

Example 3. Itaconate Production in E. coli BW25113 (DE3) Δpta-ΔldhA

To increase the availability of precursors, E. coli BW25113 (DE3) was made deficient in acetate and lactate production. Deletion of pta, encoding phosphate acetyltransferase, is known to result in accumulation of pyruvate in the cells, which may be redirected to itaconate. As Δpta strains have been reported to convert pyruvate to lactate (Castano-Cerezo et al. 2009 Microbial Cell Factories 8 doi:54 10.1186/1475-2859-8-54), this conversion was eliminated as well by deleting ldhA. To test the effect of these eliminations, the resulting strain E. coli BW25113 (DE3) Δpta-ΔldhA, containing either pEV, pKV-C, or pKV-CGA, was cultivated in pH-controlled bioreactors in MM at 30° C.

Figure 4:
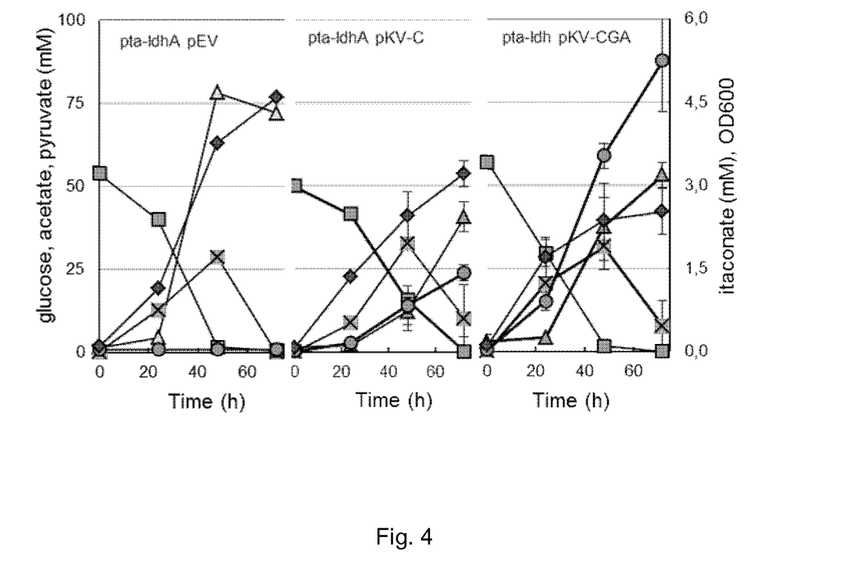
FIG. 4 shows batch cultivation of E. coli BW25113 (DE3) Δpta-ΔldhA containing pEV (left panel), pKV-C (middle panel) and pKV-CGA (right panel) in pH-controlled bioreactors on MM at 30° C. The $OD_{600}$ (diamond) and the concentrations of glucose (squares), acetate (triangles), pyruvate (crosses) and itaconate (circles) are indicated.

E. coli BW25113 (DE3) Δpta-ΔldhA (pKV-CGA) produced three times more itaconate than its wild type equivalent. Overexpression of gltA and acnA was essential to improve itaconate production, as production was not enhanced in E. coli BW25113 (DE3) Δpta-ΔldhA (pKV-C) (FIG. 4). In all E. coli BW25113 (DE3) Δpta-ΔldhA cultivations, pyruvate accumulated up to 30 mM, after which it was consumed. Acetate was still produced in the double knockout strain, but with a significant delay. Citrate and/or cis-aconitate were also observed, but at trace levels without clear correlations with strain and growth conditions (results not shown).

The results show that the simultaneous elimination of pta and ldhA and the heterologous expression of gltA and acnA increased the flux through CadA, resulting in higher itaconate titers of up to 690 mg/L, which corresponds to an itaconate yield from glucose of 0.09 mol/mol, Example 4: Effect of Δpta-ΔldhA on Growth Under Anaerobic Conditions E. coli BW25113 (DE3) (pEV) and E. coli BW25113 (DE3) Δpta-ΔldhA (pEV) were grown on MM in pH-controlled bioreactors under anaerobic conditions with glucose as carbon source. The main fermentation products of E. coli BW25113 (DE3) (pEV) were lactate, ethanol, formate and acetate (FIG. 5), which accounted for 74% of the carbon that was added to the culture (Table 3). As a lot of formate (16% Cmol) was formed in E. coli BW25113 (DE3) (pEV), only low amounts of $CO_2$ (3 mM/L, <1% Cmol) and $H_2$ (12 mM/L) were produced. The formation of acetate was redox balanced with the co-production of ethanol and succinate.

Figure 6:
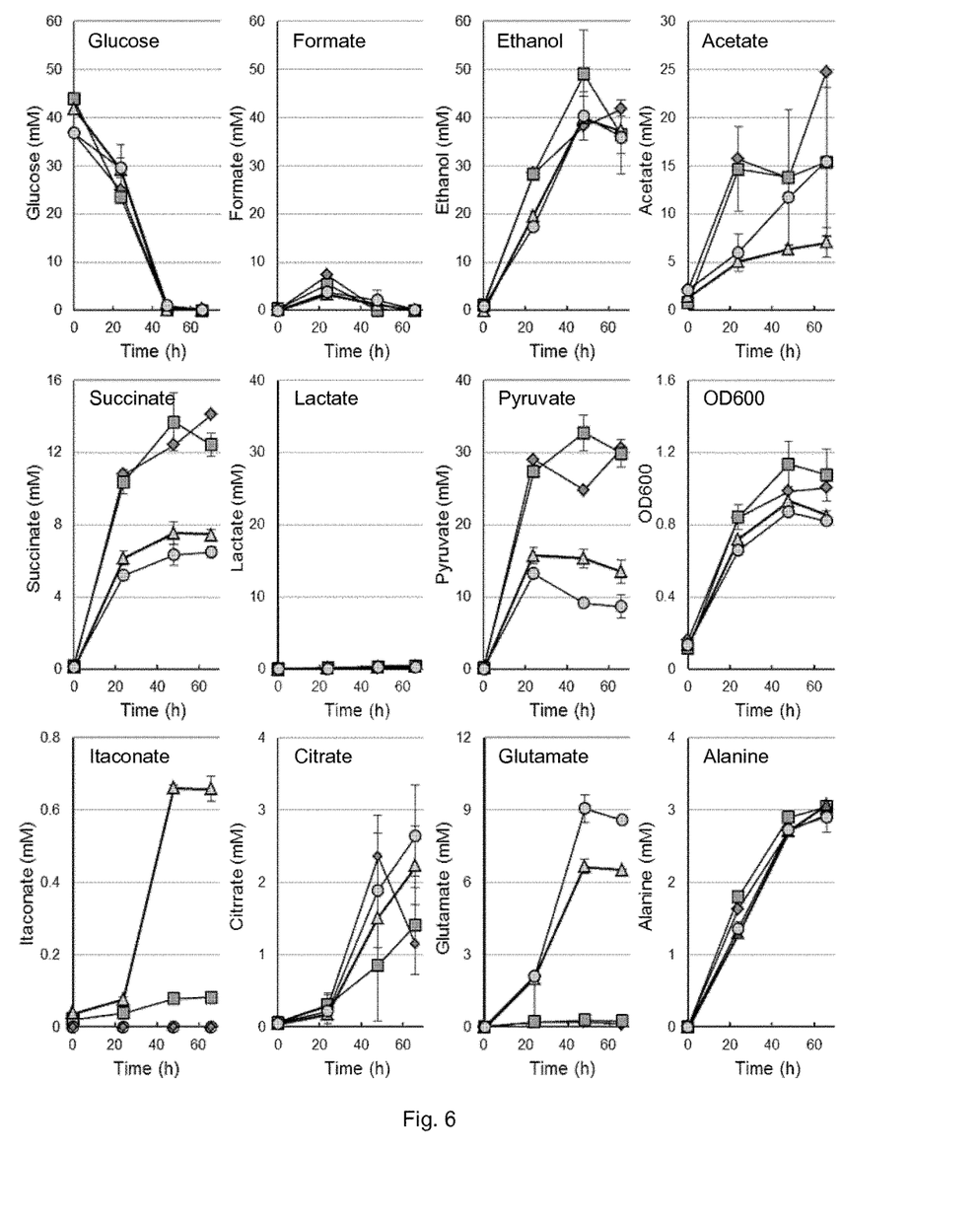
FIG. 6 shows batch cultivation of E. coli BW25113 (DE3) Δpta-ΔldhA containing pEV (diamonds), pKV-C (squares) pKV-CGA (triangles) or pKV-GA (circles) in pH-controlled bioreactors on MM at 30° C.

E. coli BW25113 (DE3) Δpta-ΔldhA (pEV), in which pta, encoding phosphate acetyltransferase, and ldhA, encoding lactate dehydrogenase were eliminated, still produced acetate in comparable amounts as E. coli BW25113 (DE3) (pEV), but lactate was no longer formed (FIG. 6; Table 3). E. coli BW25113 (DE3) Δpta-ΔldhA (pEV) did not produce formate. Instead, the production of $CO_2$ (30 mM/L, 14% Cmol) and $H_2$ (>100 mM/L) were both more than 10 times higher than observed with E. coli BW25113 (DE3) (pEV). Also pyruvate accumulated in the culture, and the amounts of succinate and ethanol were doubled. Besides, some citrate was detected.

Example 5: Itaconate Production Under Anaerobic Conditions

E. coli BW25113 (DE3) and E. coli BW25113 (DE3) Δpta-ΔldhA containing pKV-C or pKV-CGA were grown on MM in pH-controlled bioreactors under anaerobic conditions. pKV-C and pKV-CGA both express codon-optimized cadA, which encodes the cis-aconitate decarboxylase from Aspergillus terreus that was previously shown to enable the production of itaconate in E. coli. pKV-CGA also expresses citrate synthase (gltA) and aconitase (acnA) from Corynebacterium glutamicum. These genes enhanced the production of itaconate in E. coli BW25113 (DE3) Δpta-ΔldhA under aerobic conditions (see Examples 1 to 4).

Figure 5:
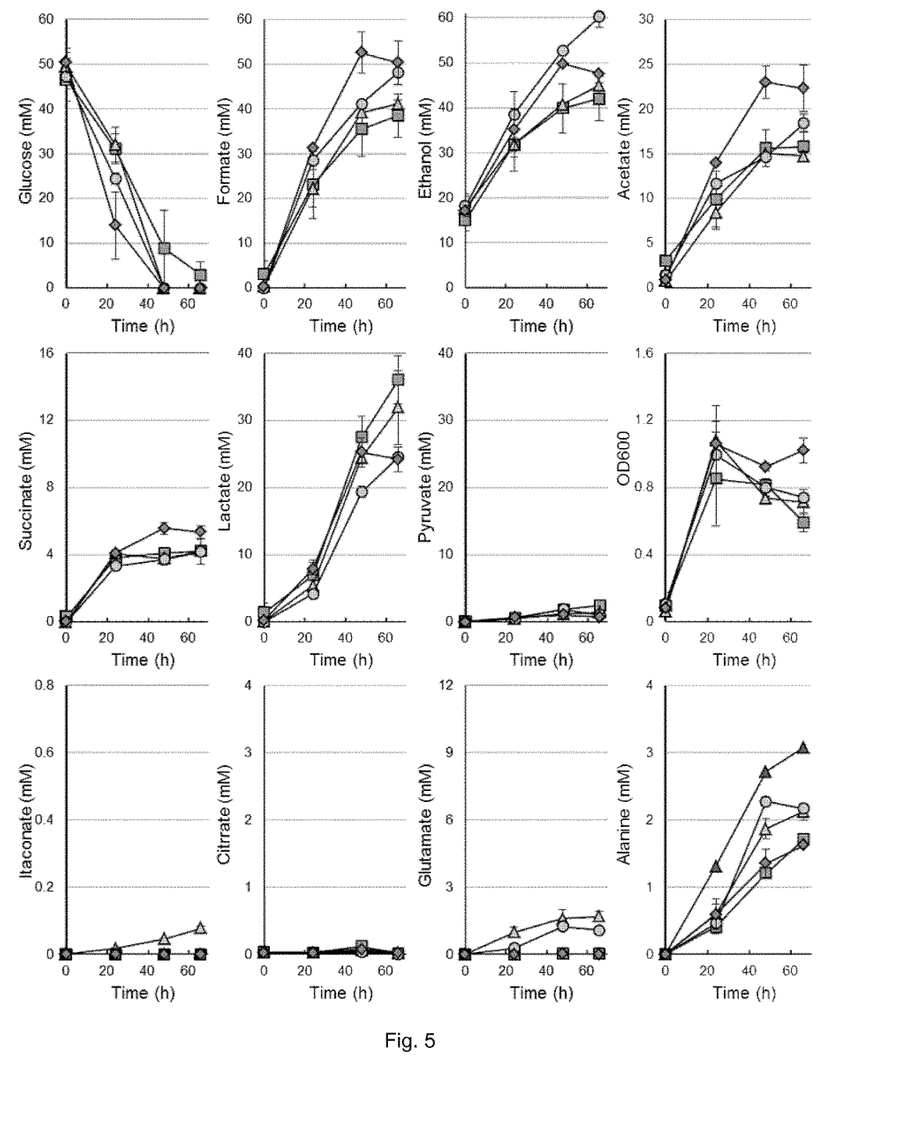
FIG. 5 shows batch cultivation of E. coli BW25113 (DE3) containing pEV (diamonds), pKV-C (squares) pKV-CGA (triangles) or pKV-GA (circles) in pH-controlled bioreactors on MM at 30° C.

Expression of cadA did not result in itaconate production in E. coli BW25113 (DE3) (pKV-C) (FIG. 5), but 0.08 mM of itaconate was produced by E. coli BW25113 (DE3) Δpta-ΔldhA (pKV-C) (FIG. 6). A similar amount of itaconate was formed by E. coli BW25113 (DE3) (pKV-CGA) (FIG. 5). E. coli BW25113 (DE3) Δpta-ΔldhA (pKV-CGA) produced eight times more itaconate (FIG. 6), showing that both the expression of gltA and acnA and the elimination of pta and ldhA stimulate the production of itaconate in E. coli under anaerobic conditions.

The fermentation products that were formed by the strains carrying either pKV-C or pKV-CGA were similar to those formed by the strains carrying pEV. However, the carbon recovery for strain E. coli BW25113 (DE3) Δpta-ΔldhA (pKV-CGA) was initially much lower (84%) than for the other strains, indicating that unidentified products were formed. Amino acid analysis of the culture supernatants showed that this strain accumulated significant amounts of glutamate and alanine. Alanine was also produced by all other strains but glutamate was only produced in large amounts by strain E. coli BW25113 (DE3) Δpta-ΔldhA (pKV-CGA). This indicates that expression of gltA and acnA increased the flux through the citric acid cycle, resulting in more itaconate and the accumulation of glutamate (FIG. 6). Carbon balances for all strains were satisfactory (90-110%), when glutamate and alanine production was taken into account (Table 3).

TABLE 3

Product distribution in % Cmol in culture supernatants of E. coli BW25113 (DE3) and E. coli BW25113 (DE3) Δpta-ΔldhA containing pEV, pKV-C, pKV-CGA or pKV-GA after 66 hours in pH-controlled bioreactors on MM at 30° C.

| | formate | ethanol | acetate | succinate | lactate | pyruvate | itaconate | citrate | glutamate | alanine | biomass | $CO_2$ | C-recovery % |
|---|---|---|---|---|---|---|---|---|---|---|---|---|---|
| E. coli BW25113 (DE3) Δpta-ΔldhA | | | | | | | | | | | | | |
| pEV | 15.8 | 20.4 | 12.8 | 6.8 | 26.7 | 1.4 | 0.0 | 0.0 | 0.0 | 1.7 | 3.0 | 0.9 | 89.5 |
| pKV-C | 14.3 | 26.2 | 11.4 | 5.3 | 33.5 | 2.3 | 0.0 | 0.5 | 0.0 | 1.5 | 2.2 | 1.4 | 98.6 |

TABLE 3-continued

Product distribution in % Cmol in culture supernatants of *E. coli* BW25113 (DE3) and *E. coli* BW25113 (DE3) Δpta-ΔldhA containing pEV, pKV-C, pKV-CGA or pKV-GA after 66 hours in pH-controlled bioreactors on MM at 30° C.

|  | formate | ethanol | acetate | succinate | lactate | pyruvate | itaconate | citrate | glutamate | alanine | biomass | CO$_2$ | C-recovery % |
|---|---|---|---|---|---|---|---|---|---|---|---|---|---|
| pKV-CGA | 13.5 | 18.7 | 9.2 | 5.9 | 37.9 | 1.9 | 0.1 | 0.0 | 2.5 | 2.3 | 2.0 | 1.1 | 95.0 |
| pKV-GA | 17.9 | 27.4 | 13.0 | 7.0 | 25.9 | 1.1 | 0.0 | 0.0 | 1.7 | 2.2 | 2.4 | 0.9 | 99.4 |
| *E. coli* BW25113 (DE3) Δpta-ΔldhA | | | | | | | | | | | | | |
| pEV | 0.0 | 23.0 | 10.4 | 18.0 | 0.1 | 20.2 | 0.0 | 2.7 | 0.2 | 3.7 | 1.8 | 14.4* | 94.4 |
| pKV-C | 0.0 | 29.7 | 5.2 | 17.6 | 0.1 | 36.0 | 0.1 | 1.5 | 0.3 | 3.5 | 3.2 | 13.2 | 110.3 |
| pKV-CGA | 0.0 | 29.8 | 3.3 | 12.1 | 0.8 | 17.9 | 1.2 | 4.0 | 13.0 | 3.6 | 2.8 | 16.4 | 104.9 |
| pKV-GA | 0.1 | 24.9 | 3.7 | 11.0 | 0.3 | 13.8 | 0.0 | 5.1 | 19.5 | 4.2 | 3.2 | 15.4 | 101.2 |

*based on theoretical CO$_2$ production

Example 6: Glutamate Production Under Anaerobic Conditions

To further investigate the production of glutamate under anaerobic conditions, gltA and acnA were expressed without cadA in *E. coli* BW25113 (DE3) and *E. coli* BW25113 (DE3) Δpta-ΔldhA. The latter strain produced eight times more glutamate than the former one, resulting in the production of 8.6 mM of glutamate. This accounts for 19.5% of the carbon that was added to the culture.

Example 7: Itaconate Production Under Nitrogen Free Conditions

Figure 7:
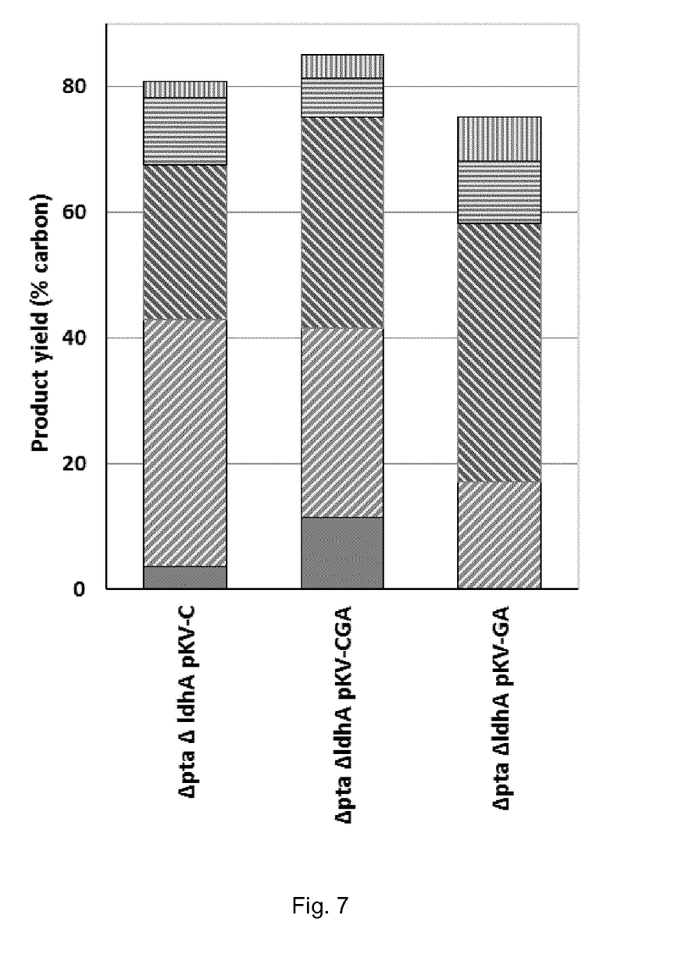
FIG. 7 shows product formation as % Cmol in E. coli BW25113 (DE3) Δpta-ΔldhA containing pKV-C, pKV-CGA and pKV-GA in nitrogen free phosphate buffer in anaerobic serum bottles after 48 hours. Itaconate (solid), pyruvate (upward diagonal stripes), ethanol (downward diagonal stripes), succinate (horizontal stripes) and other products (vertical stripes).

An option to prevent glutamate formation is to limit the availability of ammonium, as it is required for glutamate synthesis. For this, *E. coli* BW25113 (DE3) Δpta-ΔldhA containing pKV-C, pKV-CGA or pKV-GA was pre-cultured on MM in bioreactors for 48 hours. The cultures were washed and incubated in anaerobic serum bottles in nitrogen-free phosphate buffer (NF-PB) containing 60 mM glucose. The consumption of glucose and the formation of fermentation products were monitored in time. Glutamate production was completely absent in all the strains, which resulted in an increase in itaconate production up to 5.4 mM in *E. coli* BW25113 (DE3) Δpta-ΔldhA pKV-CGA (FIG. 7). This corresponds to an itaconate yield from glucose of 10.8% Cmol, which is similar to the yield obtained aerobically (9% Cmol—see Examples 1 to 4). Ethanol and pyruvate together accounted for 70-80% Cmol of the products in all strains, and pyruvate accumulation was the highest in the pKV-C strain. In addition, all strains produced 5-10% Cmol of succinate and low concentrations of formate, lactate, citrate and acetate under these conditions.

The invention claimed is:

1. A method for the production of itaconic acid, which method comprises fermenting a recombinant cell selected from a bacterial cell or a yeast cell capable of producing itaconic acid in a suitable fermentation medium, thereby to produce itaconic acid, wherein:
   (a) the recombinant cell: (i) overexpresses cis-aconitate decarboxylase; and (ii) overexpresses a part of the citric acid cycle and/or has reduced activity of a native metabolic route to acetate and/or lactate, wherein overexpression of a part of the citric acid cycle is overexpression of a citrate synthase and/or overexpression of an aconitase and wherein reduced activity of a native metabolic route to acetate is reduced activity of a phosphate acetyltransferase by deleting, disrupting or inactivating the pta gene in the recombinant cell and/or wherein reduced activity of a native metabolic route to lactate is reduced activity of a lactate dehydrogenase by deleting, disrupting or inactivating the ldhA gene in the recombinant cell; and,
   (b) the fermentation is carried out under anaerobic conditions, wherein fermentation carried out under anaerobic conditions means a fermentation process run in the absence of oxygen or in which substantially no oxygen is consumed or a fermentation process run under oxygen limited, or micro-aerobical, conditions; and
   (c) wherein glutamate production is repressed by carrying out the fermentation under nitrogen free conditions.

2. The method according to claim 1, wherein the cis-aconitate decarboxylase is an *Aspergillus terreus* cis-aconitate decarboxylase.

3. The method according to claim 1 wherein production of itaconic acid is accompanied by either ethanol and formate production or $H_2$ and $CO_2$ production.

4. The method according to claim 1, wherein the bacterial cell is *E. coli*, or wherein the yeast cell is *S. cerevisiae*.

5. The method according to claim 1 which comprises recovery of the itaconic acid.

6. A method for the production of itaconic acid, which method comprises fermenting a recombinant bacterial cell capable of producing itaconic acid in a suitable fermentation medium, thereby to produce itaconic acid, wherein:
   (a) the recombinant cell: (i) overexpresses *Aspergillus terreus* cis-aconitate decarboxylase; and (ii) overexpresses a part of the citric acid cycle and has reduced activity of a native metabolic route to acetate and lactate, wherein overexpression of a part of the citric acid cycle is overexpression of the gltA gene coding for citrate synthase and overexpression of the acnA gene coding for aconitase and wherein reduced activity of a native metabolic route to acetate is reduced activity of a phosphate acetyltransferase by deleting, disrupting or inactivating the pta gene in the recombinant cell and wherein reduced activity of a native metabolic route to lactate is reduced activity of a lactate dehydrogenase by deleting, disrupting or inactivating the ldhA gene in the recombinant cell; and,
   (b) the fermentation is carried out under anaerobic conditions, wherein fermentation carried out under anaerobic conditions means a fermentation process run in the absence of oxygen or in which substantially no oxygen is consumed or a fermentation process run under oxygen limited, or micro-aerobical, conditions; and,
   (c) wherein glutamate production is repressed by carrying out the fermentation under nitrogen free conditions.

7. The method according to claim 6 wherein the recombinant bacterial cell is a recombinant *E. coli* cell.

8. The method according to claim 6 wherein in step (a) the citrate synthase is *C. glutamicum* citrate synthase.

9. The method according to claim 6 wherein in step (a) the aconitase is *C. glutamicum* aconitase.

10. The method according to claim 6 wherein in step (b) the fermentation process is run in the absence of oxygen or in which substantially no oxygen is consumed.

* * * * *

```
                        SEQUENCE LISTING

<160> NUMBER OF SEQ ID NOS: 4

<210> SEQ ID NO 1
<211> LENGTH: 70
<212> TYPE: DNA
<213> ORGANISM: Artificial sequence
<220> FEATURE:
<223> OTHER INFORMATION: ldhA flank F primer

<400> SEQUENCE: 1
aaatattttt agtagcttaa atgtgattca acatcactgg agaaagtctt gtgtaggctg      60
gagctgcttc                                                            70

<210> SEQ ID NO 2
<211> LENGTH: 70
<212> TYPE: DNA
<213> ORGANISM: Artificial sequence
<220> FEATURE:
<223> OTHER INFORMATION: ldhA flank R primer

<400> SEQUENCE: 2
attggggatt atctgaatca gctcccctgg aatgcagggg agcggcaaga atgggaatta      60
gccatggtcc                                                            70

<210> SEQ ID NO 3
<211> LENGTH: 25
<212> TYPE: DNA
```

```
<213> ORGANISM: Artificial sequence
<220> FEATURE:
<223> OTHER INFORMATION: ldhA check F primer

<400> SEQUENCE: 3
aaatattttt agtagcttaa atgtg                                    25

<210> SEQ ID NO 4
<211> LENGTH: 25
<212> TYPE: DNA
<213> ORGANISM: Artificial sequence
<220> FEATURE:
<223> OTHER INFORMATION: ldhA check R primer

<400> SEQUENCE: 4
attggggatt atctgaatca gctcc                                    25
```